US011802199B2

(12) United States Patent
Sekiya et al.

(10) Patent No.: US 11,802,199 B2
(45) Date of Patent: Oct. 31, 2023

(54) THERMOPLASTIC FLUORORESIN TUBE

(71) Applicant: Gunze Limited, Ayabe (JP)

(72) Inventors: Kazutaka Sekiya, Konan (JP); Hiroshi Ohshima, Konan (JP); Daiki Kobayashi, Konan (JP); Masashi Kikuchi, Konan (JP)

(73) Assignee: Gunze Limited, Ayabe (JP)

( * ) Notice: Subject to any disclaimer, the term of this patent is extended or adjusted under 35 U.S.C. 154(b) by 141 days.

(21) Appl. No.: 16/959,976

(22) PCT Filed: Jul. 5, 2018

(86) PCT No.: PCT/JP2018/025442
§ 371 (c)(1),
(2) Date: Jul. 2, 2020

(87) PCT Pub. No.: WO2019/135295
PCT Pub. Date: Jul. 11, 2019

(65) Prior Publication Data
US 2020/0385561 A1    Dec. 10, 2020

(30) Foreign Application Priority Data

Jan. 4, 2018 (JP) .................................. 2018-000246

(51) Int. Cl.
*C08L 27/20* (2006.01)
*B29C 48/00* (2019.01)
(Continued)

(52) U.S. Cl.
CPC .......... *C08L 27/20* (2013.01); *B29C 48/0018* (2019.02); *C08L 27/18* (2013.01);
(Continued)

(58) Field of Classification Search
None
See application file for complete search history.

(56) References Cited

U.S. PATENT DOCUMENTS 4,510,300 A * 4/1985 Levy ..................... B29C 55/005
526/247
2004/0048020 A1   3/2004 Nanbu et al.
(Continued)

FOREIGN PATENT DOCUMENTS

FR    2067480 A5    8/1971
GB    1069690 A     5/1967
(Continued)

OTHER PUBLICATIONS

Extended European Search Report in European Patent Application No. 18898655.8, dated Aug. 17, 2021.
(Continued)

*Primary Examiner* — Nicole M. Buie-Hatcher
(74) *Attorney, Agent, or Firm* — Knobbe, Martens, Olson & Bear, LLP

(57) ABSTRACT

There is provided a thermoplastic fluororesin tube that, during the production of a catheter, can prevent a gap or air bubbles from being formed in the connection part of the catheter, and can be suitably used for the production of a catheter. A thermoplastic fluororesin tube, the thermoplastic fluororesin tube having tearability in a longitudinal direction, wherein a thermal expansion coefficient in the longitudinal direction upon heating in a gaseous phase at a temperature of 100° C. for 5 minutes is 0% or more.

6 Claims, 1 Drawing Sheet

(51) Int. Cl.
 *C08L 27/18* (2006.01)
 *B29C 61/08* (2006.01)
 *A61M 25/00* (2006.01)

(52) U.S. Cl.
 CPC .......... *A61M 25/0009* (2013.01); *B29C 61/08* (2013.01); *C08L 2203/02* (2013.01)

(56) References Cited

U.S. PATENT DOCUMENTS

| | | | |
|---|---|---|---|
| 2010/0314154 A1* | 12/2010 | Kitahara | H01B 3/307 174/110 SR |
| 2014/0255633 A1 | 9/2014 | Suzuki et al. | |
| 2016/0222145 A1 | 8/2016 | Suzuki et al. | |
| 2016/0317716 A1 | 11/2016 | Suzuki et al. | |
| 2017/0058115 A1* | 3/2017 | Suzuki | C08L 27/18 |
| 2018/0186062 A1 | 7/2018 | Kikuchi et al. | |
| 2018/0281262 A1 | 10/2018 | Kikuchi et al. | |

FOREIGN PATENT DOCUMENTS

| | | |
|---|---|---|
| GB | 1280172 A | 7/1972 |
| JP | H11-323053 A | 11/1999 |
| JP | 4968823 B2 | 1/2008 |
| JP | 2016-169856 A | 9/2016 |
| WO | WO 2013/077452 A1 | 5/2013 |
| WO | WO 2016/204174 A1 | 12/2016 |
| WO | WO 2017/043317 A1 | 3/2017 |

OTHER PUBLICATIONS

International Search Report of PCT/JP2018/025442, dated Sep. 11, 2018.

* cited by examiner

THERMOPLASTIC FLUORORESIN TUBE

TECHNICAL FIELD

The present invention relates to a thermoplastic fluororesin tube that has tearability, and is useful for the production of catheters, and a method for producing the thermoplastic fluororesin tube.

BACKGROUND ART

Conventionally, provisional covering tubes have been widely used in various articles, such as electric wires, lead wires, catheters, and guide wires. These provisional covering tubes temporarily cover these articles, and are removed therefrom after an intended purpose is achieved. Such a provisional covering tube is typically formed of a synthetic resin, a synthetic rubber, or the like.

While synthetic resins and synthetic rubbers are excellent in protection properties for articles, a large tearing force is required to remove the provisional covering tube from an article. Thus, there is the problem that it is difficult to tear the provisional covering tube by hand, such that much time is required to remove it, or a large force is applied to the article when the provisional covering tube is torn, such that the article is damaged. Moreover, a method has been employed in which the tube is torn after being scratched with a cutter or the like. In this method, however, the article inside the covering tube may be scratched with the cutter or the like.

As a technique for solving these problems, for example, Patent Literature 1 discloses a fluororesin tube having tearability, which is formed of a plurality of different fluororesins. Patent Literature 2 discloses a fluororesin tube having tearability and transparency, obtained by dispersing fine particles of PTFE in a thermoplastic fluororesin. However, both these fluororesin tubes are provided with tearability by blending other fluororesins into a main fluororesin, and thus, have a disadvantage in that increasing the amount of the other fluororesins to be blended not only reduces the heat shrinkage ratio, but also lowers transparency.

On the other hand, Patent Literature 3, for example, discloses a fluororesin tube having tearability, transparency, and high shrinkability, which is formed using one thermoplastic fluororesin. The fluororesin tube disclosed in Patent Literature 3 has the advantage of having high shrinkability and high transparency, compared with the fluororesin tubes disclosed in Patent Literatures 1 and 2.

CITATION LIST

Patent Literatures

Patent Literature 1: Japanese Patent No. 4,968,823
Patent Literature 2: WO 2016/204174
Patent Literature 3: WO 2017/043317

SUMMARY OF INVENTION

Technical Problem

As described above, Patent Literatures 1 to 3, for example, disclose fluororesin tubes that have tearability, and can be used as provisional covering tubes in the production of catheters and the like. The inventors of the present invention have conducted research on the production of catheters, by using conventional fluororesin tubes as disclosed in Patent Literatures 1 to 3.

As shown in FIG. 1, in the process for producing a catheter, the following method is typically employed: The periphery of a mandrel 20 formed of a metal core wire is covered with thermoplastic resin tubes 30 and 31 (for example, nylon-based elastomer tubes) that constitute the catheter, and the outer side of the tubes is further covered with a heat-shrinkable tube 10. In this state, this structure is fed in one direction, x1, and simultaneously passed through a heating unit 40 (about 200° C.), such that the inner diameter of the heat-shrinkable tube 10 is heat-shrunk, and the thermoplastic resin tubes 30 and 31 are melted and brought into close contact with the mandrel. As shown in FIG. 1, in the thermoplastic resin tubes that constitute the catheter, for example, the part that is gripped by a doctor by hand and the part that is inserted into the body of a patient are formed of different materials. Therefore, a plurality of tubes composed of different thermoplastic resins (for example, different in hardness) are used, as with the thermoplastic resin tubes 30 and 31.

However, in this process for producing a catheter, as shown in FIG. 1, a connection part P between the thermoplastic resin tubes 30 and 31 is connected by melting during passage through the heating unit 40; until this time, the connection part P is unconnected although the surfaces of the connection part P contact each other. Thus, a new problem has been found in that when the inner diameter of the heat-shrinkable tube 10 is heat-shrunk at the heating unit 40, a gap may be formed in the connection part P between the thermoplastic resin tubes 30 and 31, and, if these tubes are melted and connected in this state, the gap or air bubbles may be formed in the connection part P of the catheter.

It has been revealed that the conventional fluororesin tubes disclosed in Patent Literatures 1 to 3, for example, have this problem when the inner diameter is heat-shrunk.

Under such circumstances, it is a main object of the present invention to provide a thermoplastic fluororesin tube that, during the production of a catheter, can prevent a gap or air bubbles from being formed in the connection part of the catheter, and can be suitably used for the production of a catheter. It is another object of the present invention to provide a method for producing the thermoplastic fluororesin tube.

Solution to Problem

As a result of extensive research to solve the aforementioned problem, the inventors of the present invention have found that the formation of a gap or air bubbles in the connection part of a catheter is closely related to the shrinkage behavior of a thermoplastic fluororesin tube in the longitudinal direction. As a result of further research, the inventors have found that a thermoplastic fluororesin tube, the thermoplastic fluororesin tube having tearability in a longitudinal direction, wherein a thermal expansion coefficient in the longitudinal direction upon heating in a gaseous phase at a temperature of 100° C. for 5 minutes is 0% or more, can prevent, during the production of a catheter, a gap or air bubbles from being formed in the connection part of the catheter, and can be suitably used for the production of a catheter. The present invention has been completed by conducting further research based on these findings.

In summary, the present invention provides aspects of the invention as itemized below:

Item 1. A thermoplastic fluororesin tube,
the thermoplastic fluororesin tube having tearability in a longitudinal direction, wherein a thermal expansion coefficient in the longitudinal direction upon heating in a gaseous phase at a temperature of 100° C. for 5 minutes is 0% or more.

Item 2. The thermoplastic fluororesin tube according to item 1, wherein a heat shrinkage ratio of an inner diameter upon heating in a gaseous phase at a temperature of 200° C. for 5 minutes is 40% or more.

Item 3. The thermoplastic fluororesin tube according to item 1 or 2, wherein the thermoplastic fluororesin is formed of at least one of a tetrafluoroethylene-hexafluoropropylene copolymer (FEP) and a tetrafluoroethylene-perfluoroalkyl vinyl ether copolymer (PFA).

Item 4. The thermoplastic fluororesin tube according to any one of items 1 to 3, wherein the thermal expansion coefficient in the longitudinal direction upon heating at a temperature of 100° C. for 5 minutes is 0 to 4%.

Item 5. The thermoplastic fluororesin tube according to any one of items 1 to 4, which comprises a weld line in the longitudinal direction.

Item 6. A method for producing the thermoplastic fluororesin tube according to any one of items 1 to 5, comprising the steps of:

subjecting a thermoplastic fluororesin to melt extrusion molding to obtain a raw tube of the thermoplastic fluororesin tube; and expanding an inner diameter of the raw tube while heating the raw tube to a temperature lower than 140° C.

Advantageous Effects of Invention

The present invention can provide a thermoplastic fluororesin tube that, during the production of a catheter, can prevent a gap or air bubbles from being formed in the connection part of the catheter, and can be suitably used for the production of a catheter. The present invention can also provide a method for producing the thermoplastic fluororesin tube.

DESCRIPTION OF EMBODIMENTS

1. Thermoplastic Fluororesin Tube

A thermoplastic fluororesin tube of the present invention has tearability in a longitudinal direction, wherein a thermal expansion coefficient in the longitudinal direction upon heating in a gaseous phase at a temperature of 100° C. for 5 minutes is 0% or more. The thermoplastic fluororesin tube of the present invention has these properties, and thereby can prevent, during the production of a catheter, a gap or air bubbles from being formed in the connection part of the catheter, and can be suitably used for the production of a catheter.

Figure 1:
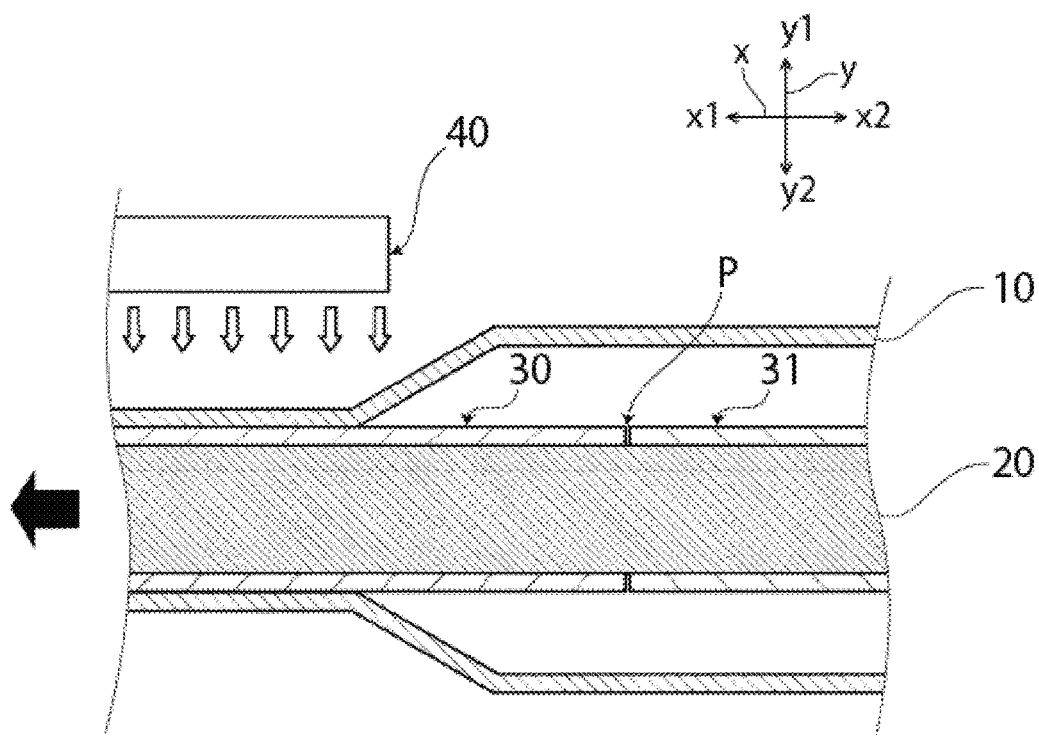
FIG. 1 is a schematic diagram for use in explaining a method for producing a catheter using a heat-shrinkable tube.

More specifically, as described above, in the thermoplastic resin tubes that constitute a catheter, as shown in FIG. 1, for example, the part that is gripped by a doctor by hand and the part that is inserted into the body of a patient are formed of different materials. Therefore, a plurality of tubes composed of different thermoplastic resins (for example, different in hardness) are used, as with the thermoplastic resin tubes 30 and 31. A connection part P between the thermoplastic resin tubes 30 and 31 is connected by melting during passage through the heating unit 40; until this time, the connection part P is unconnected although the surfaces of the connection part P contact each other. Thus, in the case of the production of a catheter using a conventional heat-shrinkable tube, when the inner diameter of the heat-shrinkable tube is heat-shrunk at the heating unit 40, a gap is formed in the connection part P between the thermoplastic resin tubes 30 and 31, and these tubes are melted and connected in this state, such that the gap or air bubbles may be formed in the connection part P of the catheter. In contrast, the thermoplastic fluororesin tube of the present invention has the property that the thermal expansion coefficient in the longitudinal direction is 0% or more in a low-temperature region at a temperature of 100° C. in an initial stage of the heat shrinkage of the inner diameter of the thermoplastic fluororesin tube (that is, the thermoplastic fluororesin tube either does not shrink in the longitudinal direction or expands in the longitudinal direction at 100° C.). Therefore, a gap or air bubbles are unlikely to be formed in the connection part P when a catheter is produced using the thermoplastic shrinkable tube of the present invention. It is presumed that when a heat-shrinkable tube has shrinkability in the longitudinal direction x1 as in the conventional ones, the thermoplastic resin tube 30 is dragged because of its shrinkage behavior such that a gap is formed in the connection part P; whereas the thermoplastic fluororesin of the present invention either does not shrink in the longitudinal direction or expands in the longitudinal direction at 100° C., and thereby can effectively prevent a gap from being formed in the connection part P due to the thermoplastic resin tube 30 being dragged. Specifically, when the thermal expansion coefficient in the longitudinal direction is above 0%, the thermoplastic resin tube 30 closer to the heating unit 40 is rather pushed opposite to the heating unit 40, such that the connection part P can be connected by melting, while ensuring that the surfaces of the connection part P between the thermoplastic resin tubes 30 and 31 contact each other. It is presumed that this can effectively prevent a gap or air bubbles from being formed in the connection part P of the catheter.

In the thermoplastic fluororesin tube of the present invention, from the viewpoint of effectively preventing, during the production of a catheter, a gap or air bubbles from being formed in the connection part of the catheter, the thermal expansion coefficient in the longitudinal direction upon heating at a temperature of 100° C. for 5 minutes is preferably 0 to 4%, more preferably above 0% and 4% or less, and still more preferably 0.3 to 4%.

The thermoplastic fluororesin tube of the present invention is formed of a thermoplastic fluororesin. The thermoplastic fluororesin is preferably a thermoplastic fluororesin that can be molded into a tubular shape by melt extrusion molding at a temperature of, for example, about 260 to 450° C., and preferably about 280 to 420° C.

Specific examples of preferred thermoplastic fluororesins include, but are not limited to, tetrafluoroethylene-hexafluoropropylene copolymers (FEP), tetrafluoroethylene-perfluoroalkyl vinyl ether copolymers (PFA), tetrafluoroethylene-ethylene copolymers (ETFE), polychlorotrifluoroethylene (PCTFE), ethylene-chlorotrifluoroethylene copolymers (ECTFE), and polyvinylidene fluoride (PVDF). In particular, a tetrafluoroethylene-hexafluoropropylene copolymer (FEP) and a tetrafluoroethylene-perfluoroalkyl vinyl ether copolymer (PFA) are preferred from the viewpoint of exhibiting particularly high tearability, and also achieving a thermal expansion coefficient in the longitudinal direction of 0% or more at a temperature of 100° C. to make the thermoplastic fluororesin tube of the present invention suitable for use in the production of a catheter. These thermoplastic fluororesins may be used alone or as a mixture of two or more. These copolymers may be ternary copolymers, for example. For example, ternary copolymers of the tetrafluoroethylene-hexafluoropropylene copolymer (FEP) include a ternary copolymer in which tetrafluoroethylene and hexafluoropropylene are additionally copolymerized with a perfluoroalkyl vinyl ether (tetrafluoroethylene-hexafluoropropylene-perfluoroalkyl vinyl ether copolymer (FEP)).

In the thermoplastic fluororesin tube of the present invention, from the viewpoint of increasing the transparency of the thermoplastic fluororesin tube, while effectively preventing a gap or air bubbles from being formed in the connection part of a catheter, the thermoplastic fluororesin tube of the present invention is preferably formed of one thermoplastic fluororesin different from polytetrafluoroethylene, particularly preferably formed of a tetrafluoroethylene-hexafluoropropylene copolymer (FEP), and more preferably formed of a tetrafluoroethylene-hexafluoropropylene-perfluoroalkyl vinyl ether copolymer.

The thermoplastic fluororesin tube of the present invention has heat shrinkability in a radial direction. The heat shrinkability of the inner diameter of the thermoplastic fluororesin tube can be favorably imparted by, for example, expanding the inner diameter by applying pressure from the inside while heating the raw tube of the thermoplastic fluororesin tube. To cover (provisionally cover) a member for producing a catheter with the thermoplastic fluororesin tube of the present invention, the member is inserted into the thermoplastic fluororesin tube having heat shrinkability, and then the thermoplastic fluororesin tube is heat-shrunk. This allows a catheter to be favorably produced, and allows the thermoplastic fluororesin tube to be favorably brought into close contact with the catheter to cover the catheter. Particularly high heat shrinkability can be imparted to the inner diameter by using, for example, a tetrafluoroethylene-hexafluoropropylene copolymer or a tetrafluoroethylene-perfluoroalkyl vinyl ether copolymer, and particularly by using a tetrafluoroethylene-hexafluoropropylene-perfluoroalkyl vinyl ether copolymer, as the one thermoplastic fluororesin that constitutes the thermoplastic fluororesin tube of the present invention.

The heat shrinkage ratio of the thermoplastic fluororesin tube of the present invention is not specifically limited, and the heat shrinkage ratio of the inner diameter upon heating in a gaseous phase (specifically in air) at 200° C. for 5 minutes is preferably 40% or more, and more preferably about 40 to 60%. In this case, the thermoplastic fluororesin tube of the present invention can be suitably used in the production of a catheter.

Moreover, as described above, the thermoplastic fluororesin tube of the present invention has the property that the thermal expansion coefficient in the longitudinal direction is 0% or more in a low-temperature region at a temperature of 100° C. in an initial stage of the heat shrinkage of the inner diameter of the thermoplastic fluororesin tube (that is, the thermoplastic fluororesin tube either does not shrink in the longitudinal direction or expands in the longitudinal direction at 100° C.). Therefore, the thermoplastic resin tube 30 closer to the heating unit 40 is not pulled toward the heating unit 40 by the thermoplastic fluororesin tube of the present invention. In the thermoplastic fluororesin tube of the present invention, the heat shrinkage ratio of the inner diameter upon heating in a gaseous phase (specifically in air) at 100° C. for 5 minutes is preferably about 10 to 30%, and more preferably about 10 to 20%.

The melt mass-flow rate (MFR) of the thermoplastic fluororesin that constitutes the thermoplastic fluororesin tube of the present invention is not specifically limited, and is preferably about 1 to 25, from the viewpoint of improving the tearability of the thermoplastic fluororesin tube, and also improving the heat shrinkability of the inner diameter. In the present invention, the MFR of the thermoplastic fluororesin is a value measured by the method in accordance with JIS K 7210: 1999.

Because the thermoplastic fluororesin tube of the present invention is formed of one thermoplastic fluororesin (excluding polytetrafluoroethylene), it can exhibit high tearability, and can also exhibit high inner-diameter heat shrinkability. A detailed mechanism by which the thermoplastic fluororesin tube of the present invention can exhibit high tearability, and can also exhibit high inner-diameter heat shrinkability, can be assumed to be as follows: Because the thermoplastic fluororesin tube of the present invention is formed of one thermoplastic fluororesin, phase separation does not occur in the fluororesin that constitutes the tube, and tearability and heat shrinkability are imparted throughout the tube with high uniformity, with the result that the tube is excellent in these properties.

Moreover, because the thermoplastic fluororesin tube of the present invention is formed of one thermoplastic fluororesin, it can also exhibit high transparency. That is, the thermoplastic fluororesin tube of the present invention can serve as a transparent thermoplastic fluororesin tube. An article, such as a catheter, that is covered with the thermoplastic fluororesin tube of the present invention is required to be disposed in the tube with high positional accuracy when it is covered with the tube. Here, the article can be easily disposed in the tube with high positional accuracy, by using the thermoplastic fluororesin tube of the present invention having high transparency. On the other hand, in the case of a tube obtained by molding a plurality of different thermoplastic fluororesins by melt extrusion into a tubular shape, or in the case of a tube formed using polytetrafluoroethylene, the tube has low transparency and is clouded, such that it may be difficult to dispose the article in the tube with high positional accuracy. In the present invention, the transparent thermoplastic fluororesin tube refers to a thermoplastic fluororesin tube that is evaluated as having high transparency in the evaluation of transparency described in the Examples.

In the thermoplastic fluororesin tube of the present invention, "one thermoplastic fluororesin" means that the number of thermoplastic fluororesins is one, from the viewpoint of imparting high tearability and high shrinkability, while preventing phase separation to maintain the inner surface smoothness and transparency. For example, the thermoplastic fluororesin may be a mixture of resins having different weight average molecular weights or different polymerization forms (such as block polymers and random polymers), or resins having different polymerization ratios of a plurality of monomers. That is, for example, even if the "one thermoplastic fluororesin" contains thermoplastic resins having different weight average molecular weights or different polymerization forms, or thermoplastic resins having different polymerization ratios of a plurality of monomers, a thermoplastic fluororesin tube having high tearability can be obtained, because phase separation is prevented as long as the number of thermoplastic fluororesins is one. However, as described above, "one thermoplastic fluororesin" as used herein does not substantially include polytetrafluoroethylene, which has poor tearability.

In the present invention, the one thermoplastic fluororesin is not required to be formed of completely one thermoplastic fluororesin only, as long as the effect of the present invention is achieved, and the one thermoplastic fluororesin may be formed of substantially one thermoplastic fluororesin.

When the thermoplastic fluororesin tube of the present invention is formed of two or more thermoplastic fluororesins, it is preferred that, for example, the content of the one thermoplastic fluororesin be 90% by mass or more, and the content of the other thermoplastic fluororesin(s) be 10% by mass or less, and more preferred that the content of the one thermoplastic fluororesin be 98% by mass or more, and the content of the other thermoplastic fluororesin(s) be 2% by mass or less. This can increase the transparency of the thermoplastic fluororesin tube of the present invention.

The thermoplastic fluororesin tube of the present invention may also contain a filler and the like, in addition to the one thermoplastic fluororesin.

In the thermoplastic fluororesin tube of the present invention, the proportion of volatile components generated upon heating at 400° C. for 1 hour is preferably 0.2% by mass or less.

The thermoplastic fluororesin tube of the present invention is preferably a thermoplastic fluororesin tube obtained by expanding the inner diameter (and the outer diameter) of the raw tube obtained by molding a thermoplastic fluororesin into a tubular shape by melt extrusion, by applying pressure from the inside to the raw tube in a heated state. In this case, during the production of a catheter, a member such as a thermoplastic resin tube that constitutes the catheter or a mandrel can be readily inserted into the thermoplastic fluororesin tube of the present invention. Moreover, because the thermoplastic fluororesin tube of the present invention has heat shrinkability, it can be heat-shrunk and favorably brought into close contact with the catheter member to cover the catheter. In the thermoplastic fluororesin tube of the present invention, specific methods for expanding the inner diameter of the raw tube include a method in which pressure is applied from the inside of the raw tube using pressurization nitrogen or the like, while the raw tube is heated to lower than 140° C., as described below. Conventionally, a temperature of about 150 to 160° C. has been employed to expand the inner diameter of the raw tube; in the present invention, however, the temperature of the raw tube when the raw tube is expanded is set to lower than 140° C., in order to cause the inner diameter to expand 0% or more in the longitudinal direction at 100° C., while causing the inner diameter to heat-shrink. While not wishing to be construed in any restricted manner, it is assumed that when the temperature of the raw tube when the raw tube is expanded is set to lower than 140° C., expansion of the raw tube gradually takes place, such that the molecular orientation in the longitudinal direction formed during the melt extrusion molding of the raw tube is likely to be relaxed, with the result that the expansion in the longitudinal direction at 100° C. is 0% or more. Because the thermoplastic fluororesin tube of the present invention obtained by expanding the inner diameter of the raw tube has improved heat shrinkability, it can cover the article more favorably by means of heat shrinkage.

In the thermoplastic fluororesin tube of the present invention, from the viewpoint of effectively preventing, during the production of a catheter, a gap or air bubbles from being formed in the connection part of the catheter, the draw-down ratio (DDR) during the melt extrusion molding of the raw tube is preferably 40 or more, and more preferably about 40 to 100, in order to eliminate the shrinkage behavior of the raw tube in the longitudinal direction, while having tearability. As used herein, DDR refers to a physical property value calculated based on the expression: DDR=[(inner diameter of extrusion die)$^2$−(outer diameter of mandrel)$^2$]/[(outer diameter of tube)$^2$−(inner diameter of tube)$^2$]. Higher DDR indicates a higher degree of molecular orientation in the longitudinal direction formed during the melt extrusion molding of the raw tube. The molecular orientation in the longitudinal direction is likely to be relaxed by expanding the inner diameter of this raw tube at a temperature in the range mentioned above.

The thermoplastic fluororesin tube of the present invention is heat-shrunk during the production of a catheter, and is subsequently torn to be peeled from the catheter. Therefore, the thermoplastic fluororesin tube of the present invention is required to have particularly high tearability when it is a thermoplastic fluororesin tube after heat-shrinkage of the inner diameter of the thermoplastic fluororesin tube of the present invention. The tearability of the thermoplastic fluororesin tube after expansion of the inner diameter of the raw tube and after heat-shrinkage of the inner diameter is intermediate between the tearability of the thermoplastic fluororesin tube before expansion of the inner diameter (that is, the raw tube) and the tearability of the thermoplastic fluororesin tube after expansion of the inner diameter and before heat shrinkage (that is, the thermoplastic fluororesin tube of the present invention), although this depends on the size after shrinkage.

The tearability of the thermoplastic fluororesin tube before expansion of the inner diameter (that is, the raw tube) is preferably such that the tear strength as measured by the below-described measurement method is 12 N/mm or less, more preferably 10 N/mm or less, and still more preferably 7 N/mm or less. The lower limit of the tear strength of the raw tube is usually 1 N/mm. Moreover, the tearability of the thermoplastic fluororesin tube of the present invention is preferably such that the tear strength as measured by the below-described measurement method is 16 N/mm or less, more preferably 14 N/mm or less, and still more preferably 11 N/mm or less. Furthermore, the tearability of the thermoplastic fluororesin tube after heat-shrinkage of the inner diameter of the thermoplastic fluororesin tube of the present invention, which, as described above, is intermediate between the tearability of the thermoplastic fluororesin tube before expansion of the inner diameter (that is, the raw tube) and the tearability of the thermoplastic fluororesin tube after expansion of the inner diameter and before heat shrinkage (that is, the thermoplastic fluororesin tube of the present invention), is, for example, preferably such that the tear strength as measured by the below-described measurement method is 14 N/mm or less, more preferably 12 N/mm or less, and still more preferably 9 N/mm or less.

(Measurement of Tear Strength)

A 40-mm cut is made in one end of a thermoplastic fluororesin tube (length 100 mm), the thermoplastic fluororesin tube is torn at a speed of 200 mm/min using a tensile tester, and the maximum force at the time is measured and defined as a tear strength (N). Measurement is performed three times, and the tearability (N/mm) of the thermoplastic fluororesin tube is determined from the weighted average of the measurements and the thicknesses of the thermoplastic fluororesin tube (2t=outer diameter−inner diameter).

The expansion ratio of the inner diameter of the raw tube is, for example, 20% or more, and preferably about 20 to 200%.

An inner diameter Wa and an outer diameter Wb (each before expansion of the inner diameter) of the raw tube of the thermoplastic fluororesin tube of the present invention are not specifically limited, and can be appropriately set according to the article to be covered. The inner diameter Wa is, for example, about 0.2 to 10 mm, and preferably about 0.2 to 5 mm. The outer diameter Wb is, for example, about 0.3 to 11 mm, and preferably about 0.3 to 6 mm.

When the thermoplastic fluororesin tube of the present invention is heat-shrunk and used, the inner diameter Wa is, for example, about 0.3 to 20 mm, and preferably about 0.3 to 10 mm, and the outer diameter Wb is, for example, about 0.5 to 25 mm, and preferably about 0.5 to 12 mm, before the thermoplastic fluororesin tube of the present invention covers the catheter member (that is, after expansion of the inner diameter and before heat shrinkage). Moreover, with respect to the thermoplastic fluororesin tube that covers the catheter (that is, after expansion of the inner diameter and subsequent heat shrinkage), the inner diameter Wa is, for example, about 0.2 to 10 mm, and preferably about 0.2 to 5 mm, and the outer diameter Wb is, for example, about 0.3 to 11 mm, and preferably about 0.3 to 6 mm.

A thickness D of the raw tube (before expansion of the inner diameter) is not specifically limited, and can be appropriately set according to the type of catheter. The thickness D is, for example, about 0.03 to 1 mm, preferably about 0.05 to 0.5 mm, and particularly preferably about 0.15 to 0.5 mm. The length of the raw tube (before expansion of the inner diameter) can also be appropriately set according to the article to be covered, and is, for example, about 0.1 m or more, and preferably about 0.1 to 2.5 m.

The thickness D of the thermoplastic fluororesin tube of the present invention (after expansion of the inner diameter and before heat shrinkage) is, for example, about 0.02 to 0.7 mm, preferably about 0.02 to 0.5 mm, and particularly preferably about 0.05 to 0.5 mm. Moreover, the thickness D of the thermoplastic fluororesin tube that covers the catheter (that is, after heat shrinkage of the inner diameter of the thermoplastic fluororesin tube of the present invention) is, for example, about 0.03 to 1 mm, preferably about 0.05 to 0.5 mm, and particularly preferably about 0.15 to 0.5 mm.

The thermoplastic fluororesin tube of the present invention preferably comprises a weld line in the longitudinal direction. In this case, the thermoplastic fluororesin tube of the present invention can exhibit particularly high tearability. In the thermoplastic fluororesin tube of the present invention, the weld line may or may not be visually observable. In the thermoplastic fluororesin tube of the present invention, usually, the weld line is not visually observable.

When the weld line is formed in the longitudinal direction of the thermoplastic fluororesin tube of the present invention, the number of the weld lines is not specifically limited; from the viewpoint of further improving the tearability, it is preferably about 1 to 10, and more preferably about 2 to 8.

When the thermoplastic fluororesin tube of the present invention comprises the weld line in the longitudinal direction, it can serve as a thermoplastic fluororesin tube that not only exhibits particularly high tearability, but also exhibits high inner-diameter heat shrinkability while having a thermal expansion coefficient in the longitudinal direction of 0% or more. That is, in the thermoplastic fluororesin tube of the present invention comprising the weld line in the longitudinal direction, even when the inner diameter of the raw tube is expanded by applying pressure from the inside of the raw tube in a heated state, cracks and the like are unlikely to be formed in the portion where the weld line is formed, and thus, the inner diameter of the raw tube can be favorably expanded. Moreover, by heating the thermoplastic fluororesin tube of the present invention having the expanded inner diameter, the inner diameter can be favorably heat-shrunk, and a thermal expansion coefficient in the longitudinal direction of 0% or more is also achieved. As a specific method for forming the weld line in the thermoplastic fluororesin tube of the present invention, for example, the method described in "2. Method for Producing Thermoplastic Fluororesin Tube" below can be employed.

The fluororesin fluorine tube of the present invention can be suitably used in the production of a catheter. It can also be suitably used for the purpose of covering (provisional covering) various articles, such as an electric wire, a lead wire, a catheter, and a guide wire. When covered with the fluororesin fluorine tube (provisional covering tube) of the present invention, the surfaces of the various articles, such as an electric wire, a lead wire, a catheter, and a guide wire, are favorably protected.

While the method for producing the thermoplastic fluororesin tube of the present invention is not specifically limited, the thermoplastic fluororesin tube of the present invention can be favorably produced by, for example, the following method.

2. Method for Producing Thermoplastic Fluororesin Tube

A method for producing the thermoplastic fluororesin tube of the present invention comprises the steps of subjecting a thermoplastic fluororesin to melt extrusion molding to obtain a raw tube of the thermoplastic fluororesin tube; and expanding an inner diameter of the raw tube while heating the raw tube to a temperature lower than 140° C.

In the method of the present invention, the thermoplastic fluororesin to be subjected to melt extrusion molding is as described in the section "1. Thermoplastic Fluororesin Tube" above.

During melt extrusion molding, the temperature at which the thermoplastic fluororesin is melted (the set temperature of the die of an extrusion molding machine) is not specifically limited as long as it is a temperature at which the thermoplastic fluororesin can be melted and molded into a tubular shape; for example, it is about 260 to 450° C., and preferably about 280 to 420° C. Moreover, when the thermoplastic fluororesin is mixed with a filler and the like and then subjected to melt extrusion molding, the filler and the like can be incorporated in the thermoplastic fluororesin tube, as described in the section "1. Thermoplastic Fluororesin Tube" above.

For melt extrusion molding, a known extrusion molding machine, for example, a single screw extruder, can be used.

Figure 2:
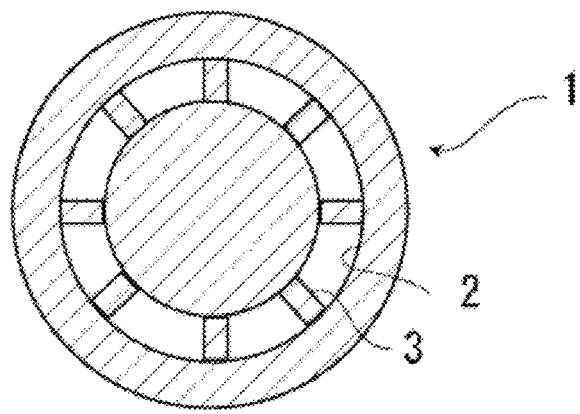
FIG. 2 is a schematic cross-sectional view (a cross section in a direction perpendicular to a melt extrusion direction, where legs are present) of one exemplary mold to be used for melt extrusion molding in a method for producing the thermoplastic fluororesin tube of the present invention.

In the method for producing the thermoplastic fluororesin tube of the present invention, it is preferred that, during melt extrusion molding, the flow path of the molten thermoplastic fluororesin be temporarily branched to form the weld line in the longitudinal direction of the raw tube, and by extension the thermoplastic fluororesin tube after expansion of the raw tube. In this case, a thermoplastic fluororesin tube having not only high tearability, but also high heat shrinkability can be obtained. More specifically, in the method of the present invention, a mold 1 having a cross section (cross section in a direction perpendicular to a direction along which the molten resin flows) as shown in, for example, FIG. 2 can be used for melt extrusion molding. With the shape of the mold 1, the flow path of the molten thermoplastic fluororesin can be temporarily branched to form the weld line in the longitudinal direction of the raw tube, and by extension the thermoplastic fluororesin tube of the present invention after expansion of the raw tube. For example, when the mold 1 having the cross section as shown in FIG. 2 is used, a plurality of legs 3 provided in a flow path 2 serve to temporarily branch the flow path of the molten thermoplastic fluororesin. The branched thermoplastic resin is protruded from the mold with the weld line formed at a merged portion, and then cooled to form the thermoplastic fluororesin tube. Therefore, when the weld line is formed using a mold having a structure in which the flow path 2 is branched by the legs 3, as in the mold 1, for example, weld lines are formed in a number that corresponds to the number of the legs 3. In the mold 1 shown in FIG. 2, eight legs 3 are provided.

This weld line can effectively improve the tearability of the thermoplastic fluororesin tube in the longitudinal direction.

Moreover, in the method of the present invention, the thermoplastic fluororesin tube of the present invention is obtained by expanding the inner diameter of the raw tube while heating the raw tube to a temperature lower than 140° C. As described above, conventionally, a temperature of about 150 to 160° C. has been employed to expand the inner diameter of the raw tube; in the present invention, however, the temperature of the raw tube when the raw tube is expanded is set to lower than 140° C. to achieve a thermal expansion coefficient in the longitudinal direction of 0% or more, even above 0%, at a temperature of 100° C., when the inner diameter of the thermoplastic fluororesin tube is heat-shrunk. The temperature (surface temperature) of the raw tube when the raw tube is expanded is preferably about 100 to 135° C., more preferably about 100 to 130° C., still more preferably about 100 to 125° C., and particularly preferably about 110 to 120° C.

Moreover, as described above, in the thermoplastic fluororesin tube of the present invention, from the viewpoint of effectively achieving a thermal expansion coefficient in the longitudinal direction of 0% or more, even above 0%, at a temperature of 100° C., to effectively prevent, during the production of a catheter, a gap or air bubbles from being formed in the connection part of the catheter, the draw-down ratio (DDR) during the melt extrusion molding of the raw tube is preferably 40 or more, and more preferably about 40 to 100.

As described above, the expansion ratio of the inner diameter of the raw tube is, for example, 20% or more, and preferably about 20 to 200%.

EXAMPLES

The present invention will be hereinafter described with reference to examples; however, the present invention is not limited to these examples.

Example 1

A thermoplastic fluororesin tube was produced by melt extrusion molding, using a tetrafluoroethylene-hexafluoropropylene-perfluoro alkyl vinyl ether copolymer (FEP, FEP-130J manufactured by Du Pont-Mitsui Fluorochemicals Co., Ltd.) as a thermoplastic fluororesin. In melt extrusion molding, a single screw extruder having a cylinder diameter of 30 mm and equipped with a mold was used to perform tube molding by a sizing plate method at a screw rotation speed of 1 rpm and a die temperature of 330° C., thereby preparing a thermoplastic fluororesin tube (raw tube, before expansion) having an inner diameter of 0.25 mm, an outer diameter of 0.85 mm, and a thickness of 0.30 mm. In the mold used, legs were provided in the flow path of the molten resin, wherein the legs each had a width of 5 mm and a length of 10 mm (length of the branched flow path), the number of the legs was 8, and the distance between a mold outlet side of the legs and the mold outlet was 10 mm. The DDR during molding was set to 90. Subsequently, the raw tube thus obtained was inserted into a cylinder with an inner diameter of 1.4 mm. The inner diameter of the raw tube was expanded while applying pressurized nitrogen, while heating the raw tube to a temperature (surface temperature) of 110° C. by blowing hot air to the surface of the raw tube. As a result, a thermoplastic fluororesin tube (after expansion) having an inner diameter of 0.92 mm, an outer diameter of 1.32 mm, and a thickness of 0.2 mm was produced.

Example 2

A thermoplastic fluororesin tube was produced as in Example 1, except that the DDR during molding of the raw tube was set to 42, and that the inner diameter of the raw tube was expanded while applying pressurized nitrogen, while heating the raw tube to a temperature of 120° C.

Example 3

A thermoplastic fluororesin tube was produced as in Example 1, except that the DDR during molding of the raw tube was set to 42.

Example 4

A thermoplastic fluororesin tube was produced as in Example 1, except that the inner diameter of the raw tube was expanded while applying pressurized nitrogen, while heating the raw tube to a temperature of 120° C.

Example 5

A thermoplastic fluororesin tube was produced as in Example 1, except that the DDR during molding of the raw tube was set to 42, and that the inner diameter of the raw tube was expanded while applying pressurized nitrogen, while heating the raw tube to a temperature of 135° C.

Example 6

A thermoplastic fluororesin tube was produced as in Example 1, except that a mixture of 98 parts by mass of a tetrafluoroethylene-hexafluoropropylene-perfluoroalkyl vinyl ether copolymer (FEP, FEP-130J manufactured by Du Pont-Mitsui Fluorochemicals Co., Ltd.) and 2 parts by mass of a tetrafluoroethylene-perfluoroalkyl vinyl ether copolymer (PFA, PFA 950HP Plus manufactured by Du Pont-Mitsui Fluorochemicals Co., Ltd.) was used as a thermoplastic fluororesin, and that the inner diameter of the raw tube was expanded while applying pressurized nitrogen, while heating the raw tube to a temperature of 120° C.

Comparative Example 1

A thermoplastic fluororesin tube was produced as in Example 1, except that the inner diameter of the raw tube was expanded while applying pressurized nitrogen, while heating the raw tube to a temperature of 150° C.

Comparative Example 2

A thermoplastic fluororesin tube was produced as in Comparative Example 1, except that the DDR during molding of the raw tube was set to 42.

Comparative Example 3

A thermoplastic fluororesin tube was produced as in Comparative Example 1, except that a mixture of 90 parts by mass of a tetrafluoroethylene-hexafluoropropylene-perfluoroalkyl vinyl ether copolymer (FEP, FEP-130J manufactured by Du Pont-Mitsui Fluorochemicals Co., Ltd.) and 10 parts by mass of a tetrafluoroethylene-perfluoroalkyl vinyl ether copolymer (PFA, PFA 950 HP Plus manufactured by Du Pont-Mitsui Fluorochemicals Co., Ltd.) was used as a thermoplastic fluororesin.

(Thermal Expansion Coefficient in Longitudinal Direction Upon Heating at 100° C.)

Each of the thermoplastic fluororesin tubes (after expansion) obtained above was heated for 5 minutes in an oven (under air) heated at 100° C. Subsequently, the lengths of the thermoplastic fluororesin tube before and after heating were measured, and a thermal expansion coefficient in the longitudinal direction was calculated based on the expression shown below. The results are shown in Table 1. It should be noted that if the length of the thermoplastic fluororesin tube after heating shrinks from the length before heating, the thermal expansion coefficient in the longitudinal direction shows a minus value.

thermal expansion coefficient (%) in longitudinal direction=[(length of thermoplastic fluororesin tube after heating)−(length of thermoplastic fluororesin tube before heating)]/(length of thermoplastic fluororesin tube before heating)×100

(Heat Shrinkage Ratio of Inner Diameter Upon Heating at 200° C.)

Each of the thermoplastic fluororesin tubes (after expansion) obtained above was heated for 5 minutes in an oven (under air) heated at 200° C. Subsequently, the inner diameters before and after heating were measured with a pin gauge, and a shrinkage ratio was calculated based on the expression shown below. The results are shown in Table 1.

heat shrinkage ratio (%) of inner diameter=[(inner diameter of thermoplastic fluororesin tube (after expansion) before shrinkage)−(inner diameter of thermoplastic fluororesin tube (after expansion and shrinkage) after shrinkage)]/(inner diameter of thermoplastic fluororesin tube (after expansion) before shrinkage)×100

(Evaluation of Tearability)

Each of the thermoplastic fluororesin tubes (after expansion) obtained above was cut to a length of 100 mm to prepare the tube after expansion for each example. Additionally, each of the thermoplastic fluororesin tubes (after expansion and shrinkage) after shrinkage obtained in (Heat Shrinkage Ratio of Inner Diameter upon Heating at 200° C.) above was cut to a length of 100 mm to prepare the tube after expansion and shrinkage for each example. Subsequently, a 40-mm cut was made in one end of each of the tube after expansion and the tube after expansion and shrinkage for each example, the tube was torn at a speed of 200 mm/min using a tensile tester, and the maximum force at this time was measured and defined as a tear strength (N). Measurement was performed three times, and the tearability (N/mm) of each of the tube after expansion and the tube after expansion and shrinkage was determined from the weighted average of the measurements and the thicknesses of each of the tube after expansion and the tube after expansion and shrinkage. The results are shown in Table 1.

(Evaluation of Transparency)

A white nylon line was inserted in the inside of each of the thermoplastic fluororesin tubes (before expansion), and observed from outside the thermoplastic fluororesin tube to evaluate transparency based on the evaluation criteria shown below. The results are shown in Table 1.

A: very high transparency; the white nylon line inside can be clearly seen through.

B: high transparency; the white nylon line inside can be seen though.

C: low transparency; the white nylon line inside cannot be seen through.

(Generation of Volatile Components Upon Heating at 400° C.)

Each of the thermoplastic fluororesin tubes (after expansion) obtained above was heated for 1 hour in an oven at 400° C., and the proportion of volatile components generated was measured. As a result, the proportion of volatile components was 0.2% by mass or less, in all the thermoplastic fluororesin tubes of Examples 1 to 6 and Comparative Examples 1 to 3.

(Production of Catheters)

As shown in the schematic diagram of FIG. 1, a catheter was produced using each of the thermoplastic fluororesin tubes (after expansion) obtained above to verify the effect of preventing, during the production of a catheter, a gap or air bubbles from being formed in the connection part of the catheter. Specifically, a polytetrafluoroethylene (PTFE)-coated SUS wire with a diameter of 0.50 was used as a mandrel, and the mandrel was covered with two nylon-based elastomer tubes (Pebax (registered trademark) tubes manufactured by Arkema Inc.) (6333 and 7233) having a length of about 30 mm, an inner diameter of 0.70 mm, and an outer diameter of 0.90 mm, and having different hardnesses. Here, the end faces of the two Pebax tubes were allowed to contact each other such that they could be connected by melting. Subsequently, the two Pebax tubes were covered with the thermoplastic fluororesin tube (after expansion), and then moved toward the heating unit at a speed of 5 mm/s and passed through the inside of a movable hot air heater (set temperature 200° C.) serving as the heating unit, which caused the thermoplastic fluororesin tube (after expansion) to shrink. As a result, a catheter in which the two Pebax tubes were connected was produced. This test was conducted 10 times (N=10) for each thermoplastic fluororesin tube (after expansion), and the number of times that a defect (a gap or air bubbles) occurred in the connection part of the two Pebax tubes having different hardnesses was measured for the obtained catheters. The effect of preventing, during the production of a catheter, a gap or air bubbles from being formed in the connection part of the catheter was evaluated based on the evaluation criteria shown below. The results are shown in Table 1.

A: the number of times that the defect occurred was 0.

B: the number of times that the defect occurred was 1 or 2.

C: the number of times that the defect occurred was 3 to 10.

TABLE 1

| | Thermoplastic fluororesin | DDR | Expansion temperature (° C.) | Heat shrinkage ratio (%) of the inner diameter at 200° C. | Thermal expansion coefficient (%) in the longitudinal direction at 100° C. | Tearability in the longitudinal direction | | Transparency | Effect of preventing, during the production of a catheter, a gap or air bubbles from being formed in the connection part of the catheter |
|---|---|---|---|---|---|---|---|---|---|
| | | | | | | Tube after expansion (N/mm) | Tube after expansion and shrinkage (N/mm) | | |
| Example 1 | FEP | 90 | 110 | 55 | 3.6 | 6.1 | 4.4 | A | A |
| Example 2 | FEP | 42 | 120 | 54 | 3.2 | 7.3 | 4.8 | A | A |
| Example 3 | FEP | 42 | 110 | 55 | 4.0 | 7.0 | 4.8 | A | A |
| Example 4 | FEP | 90 | 120 | 53 | 0.3 | 6.3 | 4.3 | A | A |
| Example 5 | FEP | 42 | 135 | 51 | 0.0 | 7.3 | 4.7 | A | B |
| Example 6 | FEP98% + PFA2% | 90 | 120 | 51 | 1.8 | 7.9 | 5.3 | B | A |
| Comparative Example 1 | FEP | 90 | 150 | 44 | −1.8 | 6.4 | 4.3 | A | C |
| Comparative Example 2 | FEP | 42 | 150 | 44 | −1.0 | 7.3 | 4.8 | A | C |
| Comparative Example 3 | FEP90% + PFA10% | 90 | 150 | 41 | −0.3 | 8.0 | 5.4 | C | C |

REFERENCE SIGNS LIST

1: mold
2: flow path
3: leg
10: heat-shrinkable tube
20: mandrel
30: thermoplastic resin tube
31: thermoplastic resin tube
40: heating unit
P: connection part

The invention claimed is:

1. A method for producing a thermoplastic fluororesin tube comprising a tetrafluoroethylene-hexafluoropropylene-perfluoroalkyl vinyl ether copolymer (FEP), the thermoplastic fluororesin tube having tearability in a longitudinal direction, wherein a thermal expansion coefficient in the longitudinal direction upon heating in a gaseous phase at a temperature of 100° C. for 5 minutes is 0% or more, the method comprising the steps of:

subjecting a thermoplastic fluororesin comprising a tetrafluoroethylene-hexafluoropropylene-perfluoroalkyl vinyl ether copolymer (FEP) to melt extrusion molding to obtain a raw tube of the thermoplastic fluororesin tube; and expanding an inner diameter of the raw tube while heating the raw tube to a temperature of from 110-135° C.

2. The method according to claim 1, wherein the thermoplastic fluororesin further comprises a tetrafluoroethylene-perfluoroalkyl vinyl ether copolymer (PFA).

3. The method according to claim 1, wherein a heat shrinkage ratio of an inner diameter of the thermoplastic fluororesin tube, upon heating in a gaseous phase at a temperature of 200° C. for 5 minutes, is 51% or more.

4. The method according to claim 1, wherein the thermal expansion coefficient in the longitudinal direction upon heating at a temperature of 100° C. for 5 minutes is 0 to 4%.

5. The method according to claim 1, which comprises a weld line in the longitudinal direction.

6. The method according to claim 1, wherein a tear strength of the thermoplastic fluororesin tube is 12 N/mm or less.

* * * * *